United States Patent

Hällgren

[11] Patent Number: 5,983,899
[45] Date of Patent: Nov. 16, 1999

[54] DIAGNOSTIC METHOD FOR ESTABLISHING FOOD INTOLERANCE/ALLERGY, AND AN INSTRUMENT FOR USE WHEN CARRYING OUT THE METHOD

[76] Inventor: Roger Hällgren, Dragontorpsvägen 9, S-740 22 Bälinge, Sweden

[21] Appl. No.: 08/750,107

[22] PCT Filed: May 26, 1995

[86] PCT No.: PCT/SE95/00602

§ 371 Date: Apr. 7, 1997

§ 102(e) Date: Apr. 7, 1997

[87] PCT Pub. No.: WO95/32668

PCT Pub. Date: Dec. 7, 1995

[30] Foreign Application Priority Data

Jun. 1, 1994 [SE] Sweden ................................. 9401883

[51] Int. Cl.⁶ ........................ A61B 19/00; G01N 33/558
[52] U.S. Cl. ........................................ 128/898; 436/513
[58] Field of Search ................................. 436/513, 518, 436/527, 541; 128/898

[56] References Cited

U.S. PATENT DOCUMENTS 5,312,343  5/1994  Krog et al. .

FOREIGN PATENT DOCUMENTS 0219461  4/1987  European Pat. Off. .

OTHER PUBLICATIONS

Allergy, vol. 44, No. 8, 1989, Nolte et al: Comparison of Intestinal Mast Cell and Basophil Histamines Release in Children With Food Allergic Reactions pp. 554–565.
Derwent's Abstract, No. 88–320634/45, week 8845, Abstract of Su, 1389759 (Ryazan Med Inst), Apr. 23, 1988.

*Primary Examiner*—David J. Isabella
*Attorney, Agent, or Firm*—Dinsmore & Shohl LLP

[57] ABSTRACT

An allergy-diagnosing method comprising analyzing a sample that has been taken rectally from the large intestine of a patient who is suspected of being allergic, after having provoked the mucous membrane of the patient's large intestine rectally with an allergen against which the suspected allergy of the patient is directed. The method is characterized by: (a) taking the sample in the lumen of the large intestine; (b) determining an inflammation marker in the sample; and (c) taking an elevated marker quantity (elevated release) as an indication that the patient is allergic to the allergen concerned. The invention also relates to an instrument for rectal insertion into the rectum. The instrument is characterized in that it has an expandable part which surrounds a central channel that opens out on each side of the expandable part, and a separate channel through which expansion of the expandable part can be controlled such that when the instrument is applied in the rectum, the outer wall of the expandable part will be in direct contact with the mucous membrane of the rectum; and in that a diffusible allergen and optionally also a receptor for an inflammation marker is/are present on the outer defining surface of the expandable part.

19 Claims, 4 Drawing Sheets

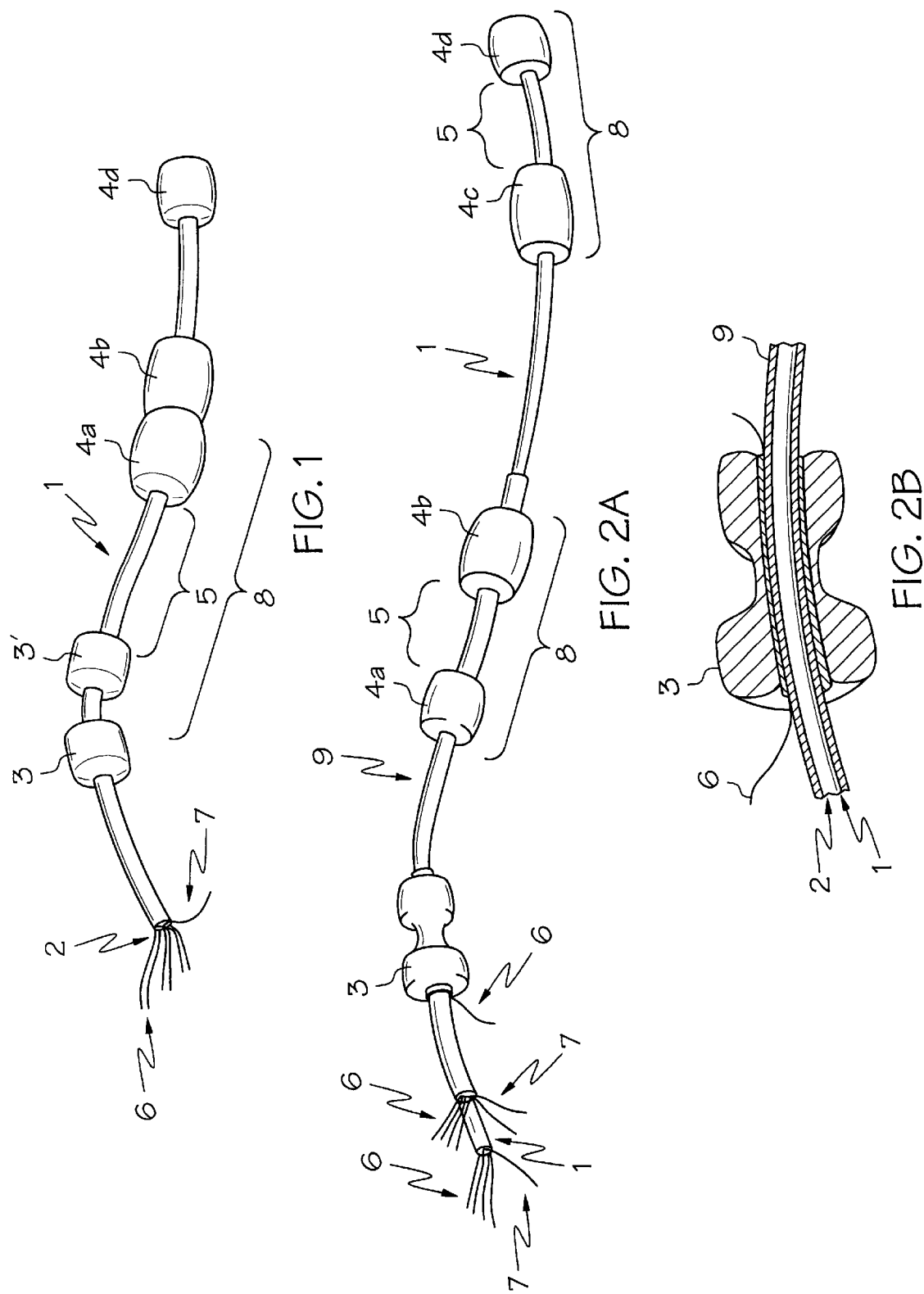

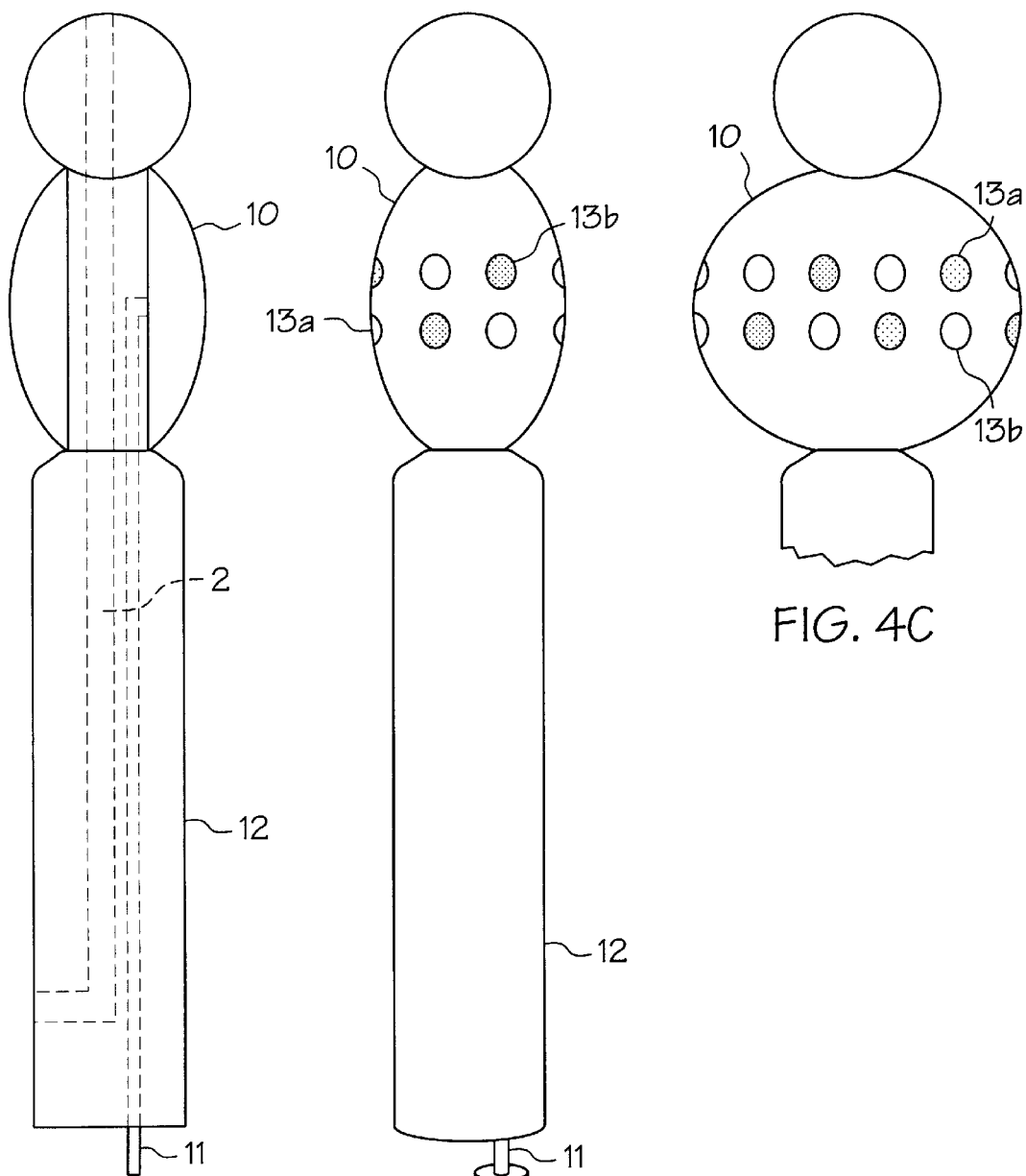

DIAGNOSTIC METHOD FOR ESTABLISHING FOOD INTOLERANCE/ALLERGY, AND AN INSTRUMENT FOR USE WHEN CARRYING OUT THE METHOD

The present invention relates to a novel method of diagnosing allergies, in particular food intolerances/allergies, and is based on the analysis of inflammation mediators (markers) that are released in the large intestine after provocation of the mucous membrane of the large intestine by the allergen. The invention also relates to a novel instrument that can be used for this type of diagnosis to provoke the mucous membrane in the large intestine. According to preferred embodiments, the instrument can be used to collect released mediators (markers) at the same time as provoking the mucous membrane.

The expression allergen in connection with the present invention is linked to discomfort in form of food intolerance/allergy. The expression is thus not imperatively linked to the discomfort being IgE mediated.

By large intestine is meant the colon and the rectum.

KNOWN TECHNIQUES OF DIAGNOSING FOOD INTOLERANCE/ALLERGY AND ASSOCIATED PROBLEMS

Present methods of diagnosing suspected food intolerance/allergy either have a limited value and/or are time-consuming. In the case of gluten intolerance, the methods are based on establishing villus atrophy in the small intestine and that the villus atrophy reverses when gluten is excluded from the diet. A guideline in this respect is found in the presence of serum antibodies against gluten. The diagnostic methods are highly deficient in respect of other forms of food intolerance/allergies. It is known from biopsy studies that gluten ingestion promotes a local inflammatory reaction in the small intestine, although there is no detailed understanding of the process. In earlier works, endeavours have been made to study the local inflammatory response of patients suffering from coeliac disease, by continuous perfusion of small intestine that has been provoked by gluten. The results show the development of a slight but significant response (B. Lavo, et al, Gut 31 (1990) 153–7; B. Lavo, et al, Am. J. Med. 87 (1989) 655–60; B. Lavo, et al, Gastroenterology 99 (1990) 703–7). The performance of small intestine perfusion, however, is technically demanding and arduous and is unsuitable for clinical diagnosis in practice.

The rectal provocation of patients suffering from coeliac disease in combination with biopsy studies has earlier been described (Dobbins, et al, Gastroenterology 47 (1964) 471–9; Austin, et al, Gut 29 (1988) 200–5; Loft, et al, Gastroenterology 97 (1989) 29–37 and Loft, et al, Lancet 335 (1990) 1293–5).

Studies have also been carried out on the basal, i.e. unprovoked, release of inflammatory mediators of patients suffering from ulcerative colitis, proctitis, Crohn's disease and other unspecified colon diseases (Y. Raab, et al, Am. J. Gastroenterology 87 (1992) 1453–9; Y. Raab, et al, Gut 34 (1993) 1203–6; and Y. Raab, et al, Digestions 55 (1994) 44–9). Samples were taken by segmental perfusion of colon and rectum. The studies were made possible with the aid of a catheter applied in the colo-rectal part of the intestine (Krog, et al, WO-A 9108013). It is alleged that the catheter concerned has a provocative function, although the method and the purpose of this provocation has not been defined.

There is thus an urgent need for a test system which will enable food intolerance/allergy to specific food substances to be established in a simple, quick and positive fashion.

BRIEF DESCRIPTION OF THE DRAWINGS

FIG. 1 illustrates a known instrument (catheter) that can be used in conjunction with the invention (Krog, et al, WO-A-9108013).

FIGS. 2a and b illustrate a further embodiment of the known instrument (catheter) and also include a sectioned view of that part which is intended to hold the instrument in place in the intestine (Krog, et al, WO-A-9108013).

FIGS. 4a, b and c illustrate an embodiment of the inventive instrument.

FIG. 5 shows the instrument of FIG. 4 applied in the rectum.

Those parts which have functional correspondence in the various Figures have been identified with the same reference signs. FIGS. 4–5 illustrate the instrument in a size suited for adult individuals.

DESCRIPTION OF THE INVENTION

We have now found that provocation per rectum with allergen induces a strong and specific local release of inflammatory mediators from large intestine mucous membrane to the lumen of patients suffering from allergy, in particular food intolerance/allergy, and which are sensibilized against the allergen concerned. Healthy individuals do not show a corresponding release.

Our discovery has led to a diagnostic method which involves analyzing a sample taken rectally from the large intestine (colon or rectum) of a patient suspected of suffering from an allergy, in particular a food allergy, after having provoked the mucous membrane in the patient's large intestine (colon or rectum) rectally with an allergen against which the suspected allergy is directed. In the broadest aspect of the invention, the method is characterized by (a) taking the sample from the lumen of the large intestine (colon and/or rectum); (b) determining an inflammation marker in the sample; and (c) taking an elevated quantity of marker (elevated release) in the sample as an indication that the patient is allergic to the allergen concerned.

The comparison is made with the normal values of healthy individuals, or with the values of the studied person taken with the same method but without simultaneous provocation.

Relevant inflammation markers are substances which derive, for instance, from neutrophilic granulocytes, eosinophilic granulocytes, mast cells/basophilic granulocytes. Specific examples are cytokines (such as IL-6 and IL-8) and myeloperoxidase (MPO), eosinophilic basic protein (ECP), eosinophilic protein X (EPX), histamine, cathepsin G, lactoferrin, lysozyme and elastase and prostaglandins. The presence of plasma proteins (e.g. albumin) in the lumen also functions as a marker, since this is indicative of leakage to the lumen.

Sampling is effected with the aid of an instrument inserted rectally into the large intestine, either solely into the rectum or also up into the colon. The instrument includes means (8) for collecting released markers and optionally also to enable perfusion and/or contact presentation of the allergen to the mucous membrane of the rectum/colon.

The means provided may be designed to enable perfusion and provocation of a given part (e.g. a segment) of the rectum/colon and to enable inflammation markers released to the lumen to be collected from this part of the rectum/colon. In order to ensure that the instrument will be kept in place in the rectum/colon, the instrument is preferably provided with a through-passing channel (2) which connects that part of the rectum/colon which lies above the instrument with that part which lies beneath said instrument. The channel functions to equalize the pressure between the surroundings and the interior of the intestine and to enable evacuation of the intestine contents. The means (8) for collection, perfusion and contact presentation are positioned on the instrument so as to lie above the internal sphincter.

Figure 3:
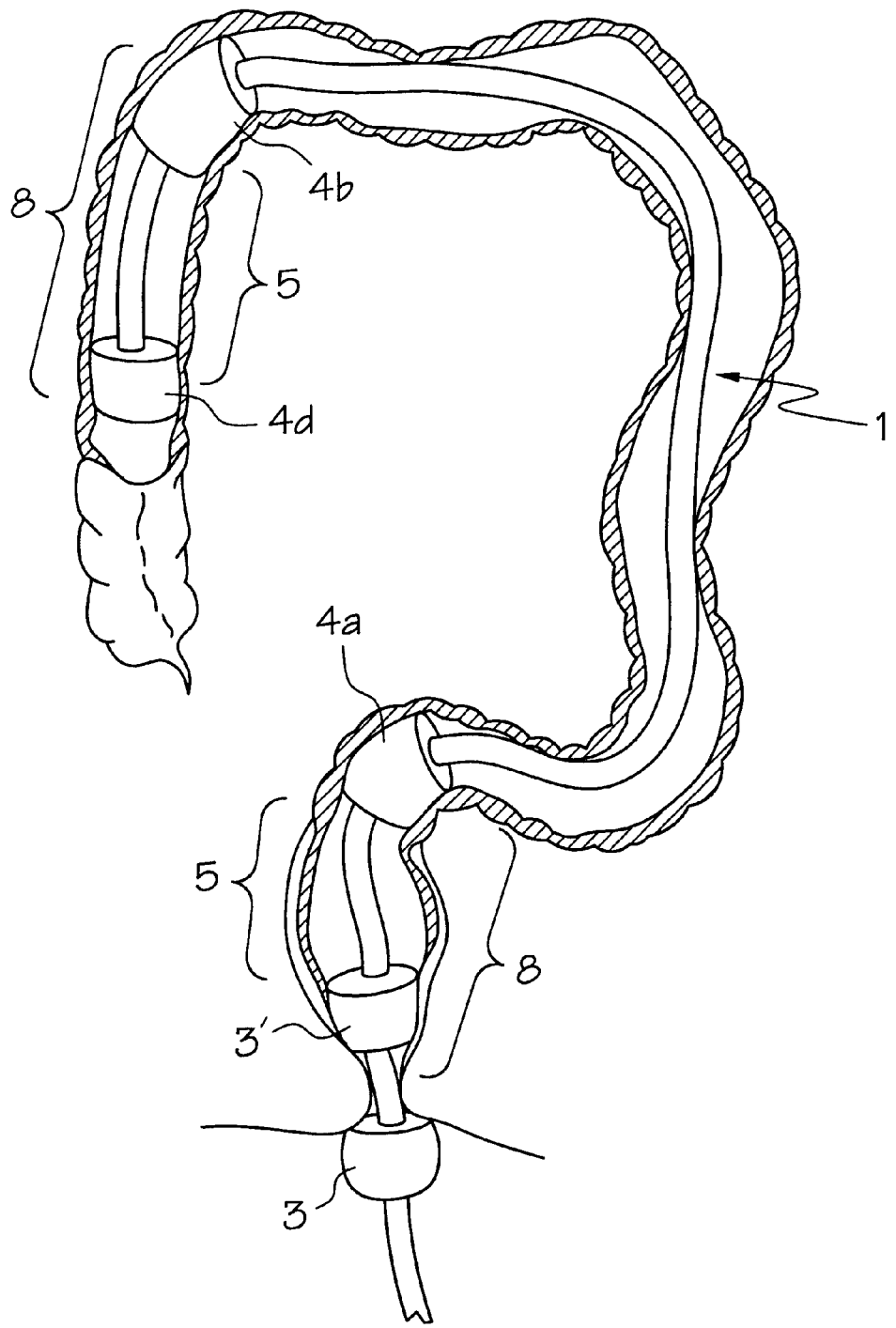
FIG. 3 shows the instrument in FIG. 1 (Krog, et al, WO-A-9108013) applied in the large intestine for provocation with the allergen and/or collection of released markers.

A suitable instrument in this regard is the catheter known and described by Krog, et al (WO-9108013) (FIGS. 1, 2 and 3). This instrument is well-suited for segmental provocation and collection of released inflammation markers by perfusion of parts of the colon and rectum of a patient. One important component of the instrument is a catheter tube (1) through which there extends a channel (2) which opens at both ends of the tube. The channel (2) functions to equalize the pressure between the intestine and the surroundings in the aforedescribed manner. One or more expandable devices (3 and 3') is/are provided around that part of the catheter which passes out through the anal orifice for affixing the catheter in the anus. Further along the catheter there is provided expandable devices (4a, b, c and d) which surround the catheter and which when expanded in the rectum/colon delimit rectal/colonic segments (5). The catheter also includes channels (6) which extend in or along the catheter wall and each of which has an opening in that part of the catheter which, when the catheter is used, is located externally of the body, and with an opening in one of the expandable devices (4) located along the catheter tube. These channels (6) function as control means for expanding the expandable devices. The catheter also includes one or more separate channels (7), each having an opening in the external part of the catheter and a further opening between those expandable devices that are intended to delimit a rectal/colonic segment. These latter channels (7) enable perfusion liquid to be conducted to/from those intestine segments (5) that are defined by two expandable devices (3' and 4a in FIG. 1, 4a and 4b, 4c and 4d respectively in FIG. 2a). Two expandable devices together with intermediate catheter segments containing a channel opening or openings thus define a means (8) which can be used for perfusion, allergen presentation and the collection of released inflammation markers. For the majority of allergens, perfusion liquid can be used both to administer allergen and to collect released inflammation markers. In the case of certain allergens, for instance gluten, which is doughy and sticky, provocation is preferably effected separately with the instrument removed from the rectum/colon. See below. An expandable device (4d in FIGS. 1 and 2a) and associated control channel should always be provided at that end of the catheter which is to be inserted furthest up into the rectum/colon.

The expandable devices may have the form of inflatable balloons.

The channels (6 and 7) extending in the catheter wall may also have the form of hoses or tubes which are fastened more or less firmly at or in the inner surface or outer surface of the catheter wall.

As illustrated in FIG. 2, greater flexibility with regard to that part of the rectum/colon to be perfused/provoked can be achieved by placing the expandable devices (4a and 4b) that are intended to define the rectal/colonic segment (5) on a tube (9) which can be pushed over the catheter tube (1). In this case, those channels (6 and 7 respectively) which lead to the expandable devices and to the spaces therebetween will preferably have the form of hoses or tubes that can be moved axially along the outer wall of the central channel. If possible, the channels may be anchored more or less firmly in the displaceable tube.

The instrument illustrated in FIGS. 1 and 2 can be used with methods that involve perfusing the rectum/colon /the whole or part thereof) initially with an allergen-free buffer, applying an aqueous allergen composition for rectal/colonic provocation, removing the allergen composition from the rectum/colon, perfusing that part of the rectum/colon that has been provoked (the second perfusion) with an allergen-free buffer solution. Perfusion liquid is collected at least during the last perfusion process for analysis of the liquid with regard to inflammation markers. The values obtained are compared with the values obtained with healthy individuals. When significantly elevated values are observed, this is taken as an indication that the individual concerned suffers food intolerance/allergy against the provocative allergen. In this variant of the invention, the instrument is removed from the colon between the first perfusion stage and the provocation stage, and is replaced prior to the second perfusion stage.

In an alternative embodiment, the allergen is included in a perfusion buffer. In this case, there is initially performed a first perfusion stage to cleanse that part of the intestine which is to be perfused. At this stage of the process, the perfusion solution is free from allergen. The intestine is then perfused with an allergen-containing perfusion solution. The intestine is finally perfused with an allergen-free perfusion solution. When practicing this alternative, the perfusion instrument need not be removed from the intestine between the different perfusion stages.

It is beneficial also to analyze the perfusion liquid from the first perfusion stage with regard to the same markers as those analyzed in the last perfusion liquid and to compare the values obtained, when practicing both of these embodiments. An elevated value in the later perfusion stage indicates an allergy to the allergen concerned.

Perfusion liquids/solutions are normally buffered, e.g. with some physiologically acceptable buffer, such as PBS. The solutions may also include sodium chloride, potassium chloride, mannitol, glucose, polyethylene glycol or other known substances which render the solutions friendly to rectal/colonic mucous.

Figure 4:
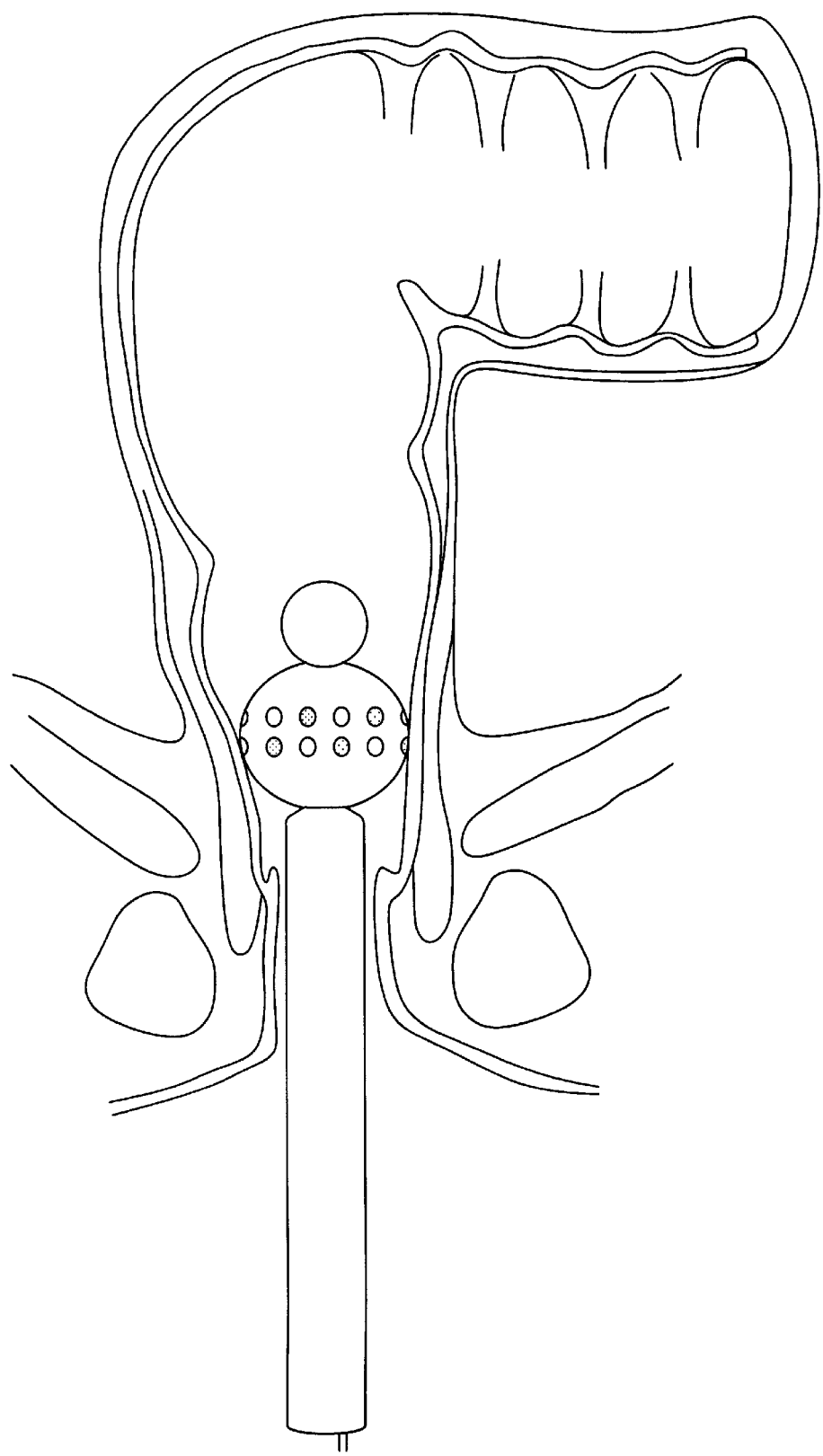

In conjunction with the invention, we have developed a novel instrument which simplifies rectal provocation and sampling processes. This instrument is shown in FIGS. 4–5 and is characterized by an expandable part/device (10) which surrounds a first channel (2) which opens on respective sides of the expandable part, and a second channel (11) through which the expansion of the expandable part (10) can be controlled such that when the instrument is applied rectally in the rectum (with the expandable part expanded), the outer wall of said expandable part will be in direct contact with the rectal mucous membrane; and in that the outer defining surface of the expandable part carries a diffusible allergen and, in the case of the preferred embodiments, optionally also a receptor for an inflammation marker. The expandable device may be placed on an insertion rod (12), to facilitate manoeuvering of the instrument. The channel (2) opening on both sides of the expandable device functions to equalize the pressure between the surroundings and the internal parts of the intestine. The expandable part (10) is shown in a non-expanded state in FIG. 4a, and in an expanded state in FIG. 4c.

The diffusible allergen is normally adsorptively or absorptively bound either to the whole surface of the outer defining surface of the expandable device, or to sub-areas (13a) thereof, as shown in FIGS. 4b and 4c. When the expandable device also exhibits bound receptors intended specifically for capturing an inflammation marker, receptor and allergen are either present on mutually the same sub-areas (13a and 13b) or on different sub-areas (13b). The receptor shall be bound to its sub-area with bonds that are capable of withstanding the conditions that prevail in the rectum, normally covalent bonds. Examples of receptors are antibodies that are specific to the marker to be captured/determined (assayed).

According to one alternative embodiment, the outer defining surface carries only receptors for one inflammation marker. No diffusible allergen is used in this case.

The material from which the expandable device of the inventive instrument is made may be the same type as that from which the expandable devices in FIGS. 1–2 are made (see Krog, et al, WO-A-9108013). The expandable device will thus have the form of an inflatable balloon, made of latex rubber, for instance. An elastic rubber ball (14) can be used to expand and empty an expandable balloon-like device.

The instrument can be readily inserted through the anus, such that the expandable devices pass beyond the internal sphincter. For practical reasons, the instrument should not be inserted further than the location at which the rectum merges with the colon in a right bend. When in a non-expanded state, the diameter of the expandable device will preferably be smaller than the diameter of the anus, i.e. smaller than 15–20 mm, with 5 mm as an optimal minimum measurement. The defining surface of the device shall reach the mucous membrane of the rectum when in an expanded state, meaning that the device shall be capable of expanding to a diameter of from 20 to 70 mm. As before mentioned, the expandable device may be an inflatable balloon. The instrument will often include an insertion rod (12) with the expandable device positioned on the forward end of the rod. The rod may have a variable length, although in order to reach fully into the rectum the rod will preferably have a minimum length of 180 mm with the addition of a further 50–100 mm which need not penetrate into the rectum. The insertion rod will include the earlier mentioned pressure equalizing channel (2) and the control channel (11) intended for controlling expansion of the expandable device. The rod may be made of PVC plastic or some like material.

The instrument is inserted to an appropriate position in the rectum of a patient, with the expandable device in a non-expanded state. The allergen diffuses to the rectal mucous membrane and, if the individual concerned is allergic to the allergen, will cause the release of inflammation markers which in turn diffuse to the lumen where they are captured (bound) by the receptor. After the marker has been released and bound to the expandable device, the device is removed and analyzed with respect to the bound marker. A value which is elevated in relation to a normal value indicates that the patient is allergic to the allergen present on the expandable device. The normal value may be a value that has been obtained with a similar instrument but with the difference that no diffusible allergen was used. A normal value may also be a value applicable to the healthy and normal population.

BEST MODE OF CARRYING OUT THE INVENTION

The best mode of carrying out the invention on the priority date of the inventive instrument is shown in FIG. 4.

The embodiment which has provided the best proof that the inventive diagnostic method functions effectively is illustrated in the experimental part of this specification. The inventor considers that the most practical embodiments of the method are those in which provocation and collection of markers released to the lumen are achieved with one and the same instrument.

EXPERIMENTAL PART

Patients

The study included nine patients suffering from coeliac disease. The diagnostic criteria were as follows:

a) Small intestine biopsy which showed subtotal or partial villus atrophy on the occasion of diagnosis.

b) Histopathological recovery after a gluten-free diet.

All biopsies were tested by one and the same pathologist without the pathologist having any prior knowledge.

Five of the patients were newly diagnosed as suffering from coeliac disease and ate a normal diet. The remaining four patients ate a gluten-free diet. Healthy volunteers, four men and one woman, who had no background of gastrointestinal sickness were used as control individuals. The control individuals had an average age of 37 years (covering a range of from 28 to 52 years of age).

Rectal perfusion

The perfusion technique employed was the technique taught by Raab, et al (Am. J. Med. 87 (1992) 1453–59) with certain modifications adopted to adapt the instrument for rectal use. In brief, there was used a six-channel PVC hose having an inner diameter of 10 mm, an outer diameter of 16 mm and a total length of 38 cm. Three inflatable balloons were fastened to the hose, to obtain a rectal perfusion segment of 8 cm in length. The channels were used either to inflate the balloons or to perfuse the segment or to administer a dye marker to the hose tip. Two rectal perfusions were performed on each individual on one and the same day: a basal perfusion and a perfusion three hours after introducing gluten (see below). The participants were studied after having fasted for 17 hours and 4 liters of an oral laxative solution (Laxabon®, TIKA, Lund, Sweden) were used as an enema. Mepiridene® 25 mg and Diazepam® 2.5 mg were administered intravenously as premedication. The intestine was studied by means of endoscopy of the rectum and of the sigmoid colon with the hose placed over the endoscope (Olympus gastroscope P2). The endoscope was placed in position and then used to guide the hose into the rectum. When the hose had been inserted to its desired position, the endoscope was withdrawn and the balloons filled with air. The volume of air used was determined partly by the reaction of the participants. The air supply was interrupted when the participants felt a light pressure in the intestine. Finally, the position of the hose was checked with the aid of a fluoroscope.

Perfusion was commenced at a rate of 3 ml/min. with the aid of a syringe pump (Model 355, Sage Instruments, Orion Research, Inc., Cambridge, Mass., U.S.A.). The perfusion buffer contained NaCl 120 mM, KCl 5.4 nM, $Na_2HPO_4$ 2 nM, glucose 10 mM, mannitol 35 mM and polyethylene glycol (PEG; MW 4 KD) 1 g/l. The buffer solution had a final pH of 7.20–7.25 and an osmolality of 290 mosm/L. The solution was maintained at a temperature of 37° C. during the perfusion stage. The collection of samples was commenced immediately the liquid cleared. Samples were taken at 20-minute intervals over a period of 80 minutes. $^{14}$C-labelled PEG (Mw 4 kD, Amersham Lab., Buckinghamshire, England), final concentration 2.3 mCi/L were added to the perfusate as a recovery determining marker. Ten milliliters of aprotilin (10,000 KIU/ml) were added per liter of perfusion buffer to inhibit proteolytic activity. To rule out the occurrence of leakage from the colon into the perfusion segment, phenol red solution (50 mg/L in physiological common salt solution) was infused proximal to the segment at a constant rate (0.5 ml/min.).

After terminating the basal perfusion process, the balloons were deflated, the hose withdrawn and the participants allowed to visit the toilet before administering a gluten enema. 135–150 minutes after introducing the gluten, the rectum-sigmodeum was rinsed with 500 ml perfusion buffer with the intention of cleansing the rectum from gluten and detritus, whereafter the perfusion hose was reinserted. The second rectal perfusion was commenced 180 minutes after gluten provocation and was continued for 180 minutes.

Provocation with gluten

Wheat gluten (6.2–6.5 g, impure wheat gluten, Sigma Chemical Co., St. Louis, Mo., U.S.A.) was suspended in 25 ml perfusion buffer. The suspension was injected into the rectum with the aid of a 60 ml syringe, with the participant lying on his/her left side. The participant was then allowed to move around as best he/she could and was instructed to hold the enema for 60 minutes.

Chemical analysis

All samples were collected on ice and 1 ml aprotilin (10,000 KIU/ml) was added to each sample (60 ml) of perfusate to inhibit the proteolytic activity. Those samples which were not analyzed immediately were frozen to $-70°$ C. $^{14}$C was determined by liquid scintillation and counting (10 min.) of samples (1 ml). Phenol red was measured spectrophotometrically at 520 nm after alkinization to pH 11, when the samples were red upon visual determination. ECP, histamine, MPO and albumin were measured in duplicate by radio-immuno assay (Pharmacia Diagnostics, Uppsala, Sweden). Prostaglandin $E_2$ was measured in duplicate by radio-immuno assay (DuPont, Dreich, Germany), IL-6 and IL-8 were measured by enzyme-immuno assay (Medgenix, Brussels, Belgium).

Statistical analysis

The results were determined as mean values +/–SD and 95% confidence interval. The statistical calculations were carried out with a Mann-Whitney U-test. When the concentration of MPO, ECP, histamine, $PGE_2$, IL-6 or IL-8 in rectal liquid was below the detection level for respective methods, the concentration was placed immediately above the detection level in the calculations (MPO=7.9 $\mu$g/L; ECP=1.9 $\mu$g/L; histamine=0.9$\mu$/L; $PGE_2$=1 $\mu$g/L; IL-6=1 $\mu$g/L; and IL-8=1 $\mu$g/L).

RESULTS

All participants in the study were able to manage the rectal perfusion and none of the participants developed symptoms due to gluten provocation. The provocation induced an increase in the release of inflammation markers, this increase being 25-fold for markers from neutrophilic granulocytes (e.g. myeloperoxidase), on average 3-fold for eosinophilic basic protein (from eosinophiles) and for $PGE_2$, on average 7-fold for cytokines (e.g. IL-6 and IL-8) and in the case of some participants up to a 20-fold increase for histamine (marker for mast cells/basophils). In the case of those participants/patients suffering from coeliac, gluten provocation in the rectum resulted in more than a 4-fold increase in mucous leakage, defined as the release of plasma proteins (albumin) to the rectal lumen.

I claim:

1. An allergy diagnostic method, comprising provoking rectally the mucous membrane in the large intestine of a patient suspected of suffering from an allergy with an allergen against which the suspected allergy is directed, taking a sample rectally from the lumen of the large intestine of said patient, and analyzing said sample to determine an inflammation marker in the sample, wherein an elevated marker quantity is an indication that said patient is allergic to the allergen.

2. A method according to claim 1, wherein the marker derives from neutrophilic granulocytes, eosinophilic granulocytes, mast cells or basophilic granulocytes, or comprises a cytokine, a prostaglandin or a plasma protein.

3. A method according to claim 1, wherein the marker comprises myeloperoxidase, eosinophilic basic protein, histamine, a cytokine, or a prostaglandin.

4. A method according to claim 1, comprising provoking only a part of the large intestine.

5. A method according to claim 1, comprising taking the sample with the aid of an instrument which is inserted rectally into the large intestine and which includes means which enable the collection of released markers.

6. An instrument for rectal insertion into the rectum, wherein the instrument has an expandable part which surrounds a central channel which opens out on each side of the expandable part, and a separate channel through which expansion of the expandable part can be controlled such that when the instrument is applied in the rectum, the outer wall of the expandable part will be in direct contact with the mucous membrane of the rectum; and wherein a diffusible allergen and optionally also a receptor for an inflammation marker is/are present on an outer defining surface of the expandable part.

7. An instrument according to claim 6, wherein the allergen comprises animal proteins, vegetable proteins or their partially hydrolyzed allergen fragments.

8. An instrument according to claim 6, wherein the receptor is directed towards a substance comprising inflammation markers from neutrophilic granulocytes, from eosinophilic granulocytes, or from mast cells or basophilic granulocytes, or comprising cytokines or plasma proteins.

9. An instrument according to claim 6, wherein the receptor is directed towards myeloperoxidase, eosinophilic basic protein, histamine, a cytokine, a prostaglandin or a plasma protein.

10. A method according to claim 2, wherein the marker comprises albumin.

11. A method according to claim 3, wherein the marker comprises IL-6, IL-8 or $PGE_2$.

12. An instrument according to claim 11, wherein the allergen comprises gluten, milk protein or soja bean protein.

13. An instrument according to claim 11, wherein the receptor is directed toward IL-6, IL-8, $PGE_2$ or albumin.

14. An allergy diagnostic method, comprising provoking rectally the mucous membrane in the large intestine of a patient suspected of suffering from an allergy with an allergen against which the suspected allergy is directed, taking a sample rectally from the lumen of the large intestine of the patient, and analyzing the sample to determine an inflammation marker in the sample, wherein an elevated marker quantity is an indication that the patient is allergic to the allergen; further wherein the sample is taken with the aid of an instrument including means which enable profusion of all or a part of the large intestine and means which enable the collection of released markers, and by inserting the instrument rectally into the large intestine, first perfusing part of the large intestine initially with an allergen-free buffer, removing the instrument, applying an aqueous allergen composition for provocation in the large intestine, removing the allergen composition from the large intestine, re-applying the instrument in the large intestine, and second profusing the part of the large intestine which has been provoked with an allergen-free buffer solution, in which stages the profusion solution for at least the second profusion is collected for analysis with regard to inflammation markers.

15. An allergy diagnostic method, comprising provoking rectally the mucous membrane in the large intestine of a patient suspected of suffering from an allergy with an allergen against which the suspected allergy is directed, taking a sample rectally from the lumen of the large intestine of the patient, and analyzing the sample to determine an inflammation marker in the sample, wherein an elevated marker quantity is an indication that the patient is allergic to the allergen; further wherein the sample is taken with the aid of an instrument including means for profusion and contact presentation of the allergen to a part of the mucous membrane of the large intestine and means for collecting released markers, and by inserting the instrument rectally into the large intestine, initially profusing part of the large intestine with an allergen-free buffer, profusing the same part of the large intestine a second time with an aqueous allergen composition for provocation in the large intestine, and finally profusing the same part of the large intestine for a third time with an allergen-free buffer, in which stages the profusion solution used at least in the third profusion is collected for analysis with respect to an inflammation marker.

16. An allergy diagnostic method, comprising provoking rectally the mucous membrane in the large intestine of a patient suspected of suffering from an allergy with an allergen against which the suspected allergy is directed, taking a sample rectally from the lumen of the large intestine of the patient, and analyzing the sample to determine an inflammation marker in the sample, wherein an elevated marker quantity is an indication that the patient is allergic to the allergen concerned; further wherein the sample is taken with the aid of an instrument which is inserted rectally into the large intestine and which comprises an expandable part surrounding a central channel which opens out on each side of the expandable part, and a channel through which expansion of the expandable part can be controlled such that when the instrument is applied rectally in the large intestine, the outer wall of the expandable part will be in direct contact with the mucous membrane of the large intestine, wherein a diffusible allergen and optionally also a receptor for the inflammation marker are present on an outer defining surface of the expandable part, and means which enable the collection of released markers.

17. A method according to claim 1, for diagnosis of food allergy.

18. A method according to claim 14, wherein the perfusion liquids from the first and the last perfusion process are collected as separate samples and are analyzed with respect to an inflammation marker, and wherein an elevated concentration in the perfusion liquid from the last perfusion process relative to the concentration of the same marker in the same initial perfusion process is taken as an indication that the perfused person is intolerant or allergic to the provocative allergen used.

19. A method according to claim 16, wherein the allergen is present on a plurality of part-surfaces on the outer surface of the expandable part; and wherein a receptor for the inflammation marker is present on other part-surfaces of the outer surface of said expandable part.

\* \* \* \* \*

UNITED STATES PATENT AND TRADEMARK OFFICE
CERTIFICATE OF CORRECTION

PATENT NO. : 5,983,899
DATED : November 16, 1999
INVENTOR(S) : Roger Hällgren

It is certified that error appears in the above-identified patent and that said Letters Patent is hereby corrected as shown below:

Claim 14, column 8, line 61, change "profusion" to --perfusion--.

Claim 14, column 9, line 3, change "profusing" to --perfusing--.

Claim 14, column 9, line 5, change "the profusion" to --the perfusion--.

Claim 14, column 9, lines 5-6, change "profusion" to --perfusion--.

Claim 15, column 9, line 17, change "profusion" to --perfusion--.

Claim 15, column 9, line 25, change "profusing" to --perfusing--.

Claim 15, column 9, line 27, change "profusion" (both occurrences) to --perfusion--.

Signed and Sealed this

Eighteenth Day of July, 2000

Attest:

Q. TODD DICKINSON

Attesting Officer

Director of Patents and Trademarks